United States Patent [19]

Jolly

[11] Patent Number: Plant 6,561

[45] Date of Patent: Jan. 24, 1989

[54] MINIATURE ROSE PLANT NAMED 'PROUD HERITAGE'

[76] Inventor: Nelson F. Jolly, P.O. Box 188, Gregg Neck Rd., Galena, Md. 21635

[21] Appl. No.: 32,433

[22] Filed: Mar. 30, 1987

[51] Int. Cl.[4] ..... A01H 5/00

[52] U.S. Cl. ..... Plt./10

[58] Field of Search ..... Plt./7–10

*Primary Examiner*—James R. Feyrer

[57] ABSTRACT

A new and distinct variety of rose plant of the miniature rose class, which was originated by my crossing Little Rascal as seed parent and Chris Jolly as pollen parent; characterized by its strong upright growing habit and deep crimson red, well-formed blooms which do not fade or lose their strong substance when cut.

1 Drawing Sheet

1

The present invention relates to a new and distinct variety of rose plant of the miniature rose class, which was originated by my crossing as seed parent the rose known as "Little Rascal" and the rose known as "Chris Jolly" as pollen parent.

Among the novel characteristics possessed by this new variety which distinguished it from all other varieties of which I am aware are:

1. The deep crimson flowers are larger than the average miniature rose, reaching to 2–2½" when fully opened and retaining a uniform crimson color at all stages of opening.

2. One of the newer large-sized miniature roses we have bred for the pot-forced market. Excellent for low beds and cutting gardens.

3. Vigorous upright growing plant grows reaching a height of 18–24", having large deep-green thick foliage with strong canes, and making it a good background plant in the miniature rose garden.

Asexual reproduction by budding of the new variety as performed in Kent County, Md. shows that the foregoing and other distinguishing characteristics come true to form and are established and transmitted through succeeding propagation.

The new and improved rose variety which I have developed is an unusual dark crimson red miniature rose that holds its deep uniform color from bud to mature bloom and also upon aging. The flower has many ovid petals, recurling to a flat open flower with petals recurling to a shingle-like formation reflecting the deep crimson red color at the heart of each flower and revealing the velvet appearance of each thick petal.

The accompanying drawing shows typical specimens of the vegetative growth and flowers of the new variety in different stages of development and as depicted in color as nearly true as it is reasonably possible to make the same in a color illustration of this character.

The following is a detailed description of my new variety named "Proud Heritage" (Joulproud), with color terminology in accordance with the Royal Horticultural Society Colour Chart (RHSCC). The terminology used in color description herein refers to plate numbers in the aforementioned color chart, e.g., "47-A" is plate 47-A of the Royal Horticultural Society Colour Chart.

Parentage: Seedling. p2 *Seed parent.*—"Little Rascal".
*Pollen parent.*—"Chris Jolly".
Class: Miniature.

2

The following observations are made of specimens grown outdoors at Kent County, Md., during the month of July.

FLOWER

Blooming habit: Continuous.

A. Bud:
- (1) *Size.*—Large.
- (2) *Form.*—Exhibition.
- (3) Color.—When sepals first divide — near 47-A; when colors begin to unfurl — 47-B; when half-blown, inside of petals — 47-B; 46-A on reverse.
- (4) *Sepals.*—½ cm. shorter than the bud.
- (5) *Peduncle.*—Length 4½ cm. Aspect — straight. Strenth — medium heavy. Color. — 143-B.

B. Bloom:
- (1) *Size.*—2–2¼.
- (2) *Borne.*—Singly.
- (3) *Form.*—High centered, bell-shaped.
- (4) *Petalage.*—21–24.
- (5) *Color.*—During first two days. Center of flower — deep red, 46-B. Outer petals — near 47-A. Base of petals: 47-A. Reverse of petals — near 46-B.
- (6) *Color change.*—General tonality from a distance is deep crimson red. Lightens slightly in the center as bloom ages. Finishes to 46-A after three or more days.

C. Petals:
- (1) *Texture.*—Thick.
- (2) *Appearance.*—Satiny.
- (3) *Form.*—Broad teardrop.
- (4) *Arrangement.*—Regularly arranged shingle-like overlay.
- (5) *Petaloids in center.*—Few.
- (6) *Persistence.*—Drops off cleanly.
- (7) *Fragrance.*—Good.
- (8) *Lasting quality.*—5–6 days on plant, 5–7 days as cut flower.

REPRODUCTIVE ORGANS

A. Stamens, anthers: Regularly arranged around styles.
- (1) *Color.*—Yellow-orange, near to 17-A.

B. Pollen: Color is yellow-orange, near to 17-C.

C. Styles: Medium length and even.

D. Stigmas:
- *Color.*—Yellow-orange — 19-D.

E. Hips: Globular, 1.75–2.00 cm., green 138-B, changing to orange at maturity. Seeds protrude.

PLANT

A. Form: Upright.
B. Growth: Very vigorous.
Height attained.—24–28 cm.
C. Foliage: Compound of 5 leaflets.
(1) *Size.*—Medium.
(2) *Quantity.*—Abundant.
(3) *Color.*—New foliage: upper side —187-A, under side — 178-A. Old foliage: — 141-A, under side — 138-A.
(4) *Shape.*—Oval, pointed.
(5) *Texture.*—Upper side — smooth. Under side — rough.
(6) *Edge.*—Serrated.
(7) *Serration.*—5 per cm.
(8) *Leaf stem.*—Color — 138-A; under side — 138-B.
(9*Stipules.*—Short, slightly bearded.
D. Wood:
(1) New wood.—Color — 138-B. Bark — smooth.

(2) *Old wood.*—Color — 139-D. Bark — smooth.
E. Thorns:
(1) *Thorns.*—Quantity: on main stalks from base — few; on laterals from stalk — few. Form: flat base, slightly hooked. Length: medium. Color when young — 137-C. Position: irregular.
(2) *Prickles.*—Quantity: On main stalks — none; on laterals — none.
F. Plant's disease resistance:
(1) *Mildew.*—Moderate.
(2) *Blackspot.*—Moderate.
(3) *Rust.*—None observed.
G. Winter hardiness: Good winter hardiness.

I claim:

1. A new and distinct variety of rose plant of the miniature rose class, substantially as shown and described, characterized particularly by dark crimson well-formed blooms that hold their color throughout the life of the flower; strong upright growing plant, taller than the average miniature with well-formed 2" flowers that cover the complete plant.

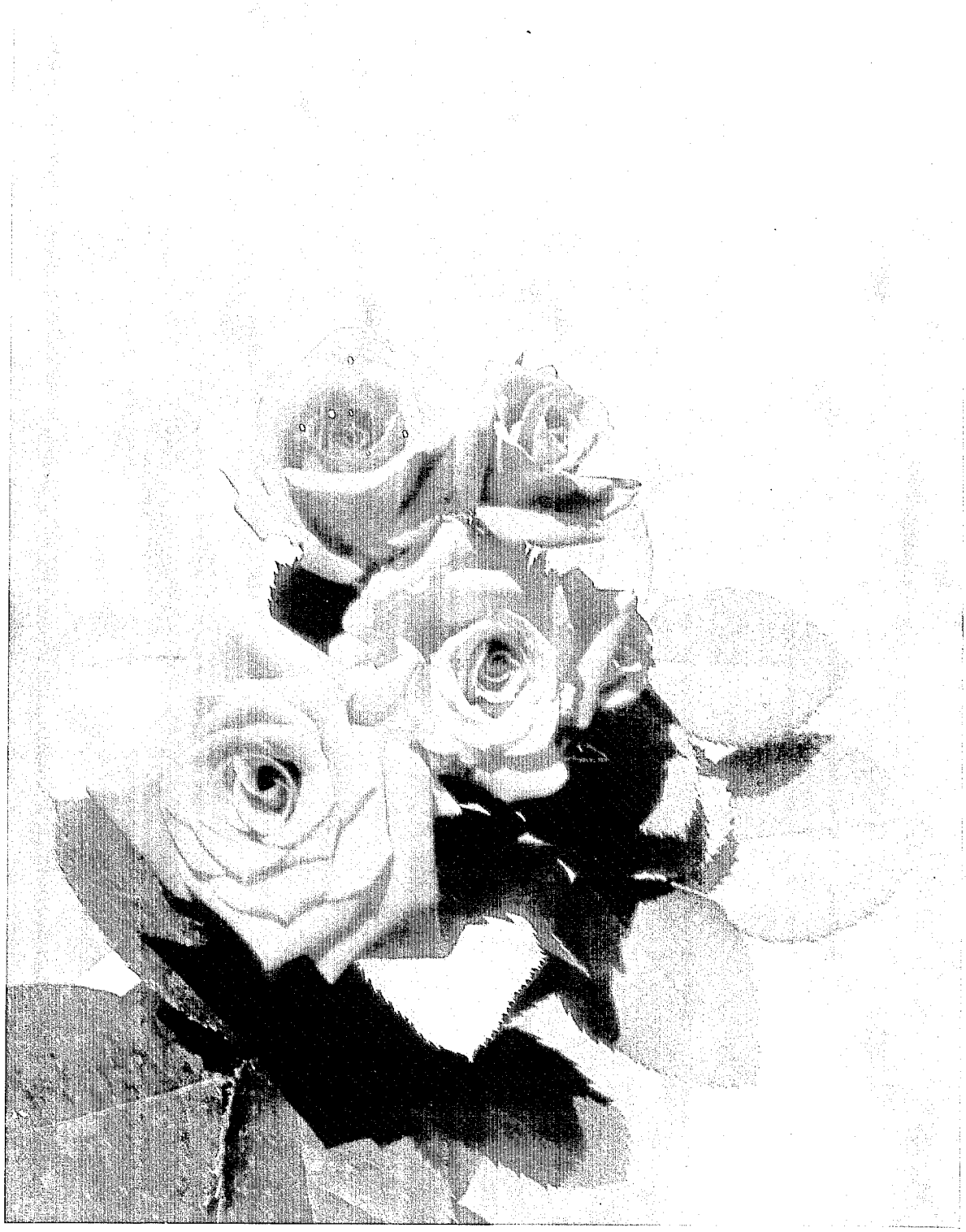

* * * * *